(12) United States Patent
Blaylock et al.

(10) Patent No.: US 8,881,999 B2
(45) Date of Patent: Nov. 11, 2014

(54) FRAGRANCE DIFFUSION SYSTEM

(75) Inventors: Robert David Blaylock, Tega Cay, SC (US); John Thurston Chandler, Charlotte, NC (US); Tom Conroy, Newton, CT (US)

(73) Assignee: ScentAir Technologies, Inc., Charlotte, NC (US)

( * ) Notice: Subject to any disclaimer, the term of this patent is extended or adjusted under 35 U.S.C. 154(b) by 358 days.

(21) Appl. No.: 13/180,051

(22) Filed: Jul. 11, 2011

(65) Prior Publication Data

US 2012/0018530 A1 Jan. 26, 2012
US 2012/0261484 A2 Oct. 18, 2012

Related U.S. Application Data

(60) Provisional application No. 61/366,027, filed on Jul. 20, 2010.

(51) Int. Cl.
*A61M 11/06* (2006.01)
*A61L 9/12* (2006.01)
*A61L 9/14* (2006.01)

(52) U.S. Cl.
CPC . *A61L 9/14* (2013.01); *A61L 9/122* (2013.01); *A61L 2209/133* (2013.01)
USPC ........... 239/338; 239/337; 239/351; 239/372; 239/432; 261/30; 261/64.3; 261/69.1; 422/124

(58) Field of Classification Search
USPC ............ 239/337, 338, 351, 372, 432; 261/30, 261/52, 55, 56, 64.3, 69.1; 422/124
See application file for complete search history.

(56) References Cited

U.S. PATENT DOCUMENTS

| | | | | |
|---|---|---|---|---|
| 2,686,944 | A * | 8/1954 | Gubelin | 422/124 |
| 4,383,951 | A * | 5/1983 | Palson | 261/30 |
| 4,396,557 | A * | 8/1983 | DeLuca | 261/30 |
| 5,030,253 | A * | 7/1991 | Tokuhiro et al. | 95/216 |
| 6,592,104 | B2 * | 7/2003 | Cox | 261/26 |
| 7,651,077 | B1 | 1/2010 | Rosener et al. | |
| 7,913,933 | B2 * | 3/2011 | Van Roemburg | 239/338 |
| 2005/0224596 | A1 | 10/2005 | Panopoulos | |
| 2007/0163557 | A1 | 7/2007 | Layher et al. | |
| 2008/0223953 | A1 | 9/2008 | Tomono et al. | |
| 2011/0089252 | A1 | 4/2011 | Rosener et al. | |

FOREIGN PATENT DOCUMENTS

| WO | WO8808721 A1 | 11/1988 |
|---|---|---|
| WO | WO2005105163 A1 | 11/2005 |
| WO | WO2009059373 A1 | 5/2009 |

OTHER PUBLICATIONS

European Search Report for Application No. 11174020.5-2113 dated Oct. 5, 2011, 5 pages.

* cited by examiner

*Primary Examiner* — Dinh Q Nguyen
(74) *Attorney, Agent, or Firm* — Fish & Richardson P.C.

(57) ABSTRACT

A system for fragrancing air includes an adjustable fan that is used to generate an air flow to push atomized fragrance oil from an output orifice of the system. The fragrance in the air is generated from atomized fragrance oil, where liquid fragrance oil can be stored in a cartridge bottle assembly and then atomized with compressed air in a collector assembly in the system. When the system is mounted on a wall or ceiling, the adjustable fan can be used to direct the fragrance downward at any number of angles from the system. The system can be programmed to adjust a fan speed and various settings of the fragrance delivery.

29 Claims, 14 Drawing Sheets

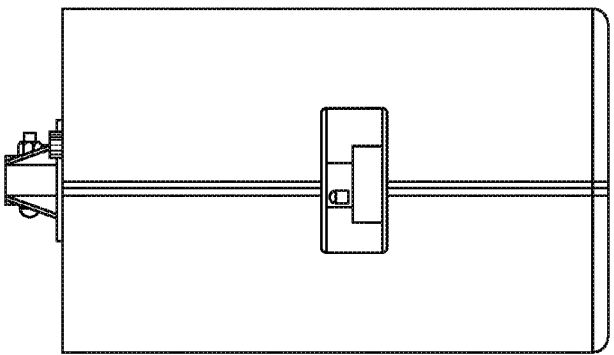
FIG. 1A
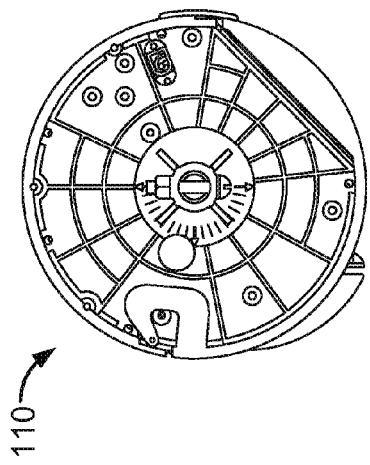
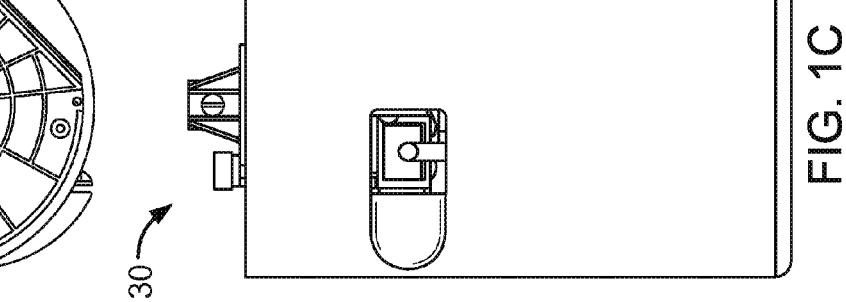
FIG. 1C
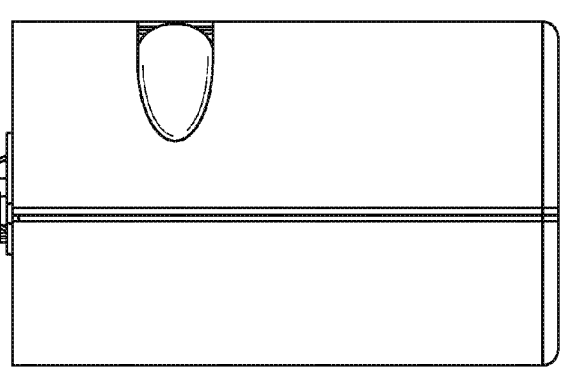
FIG. 1D
FIG. 1B

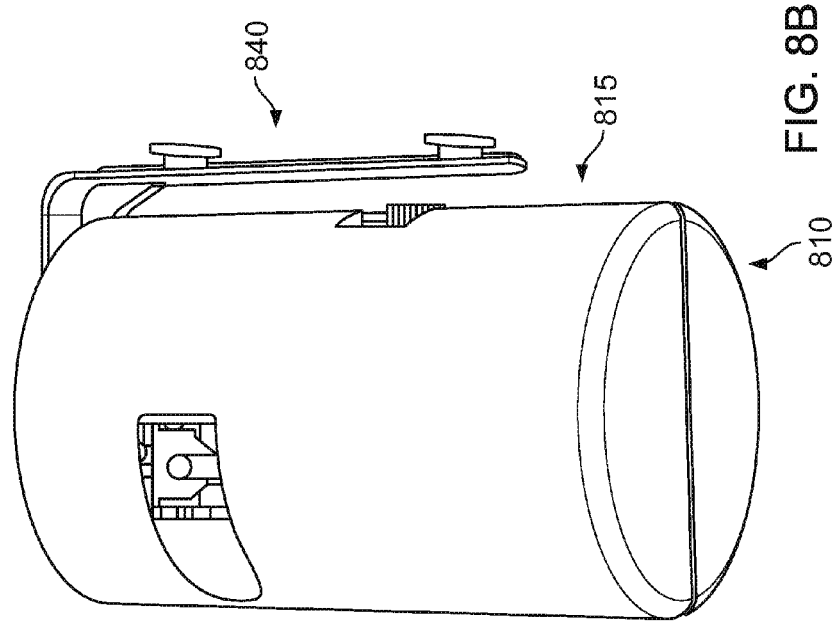
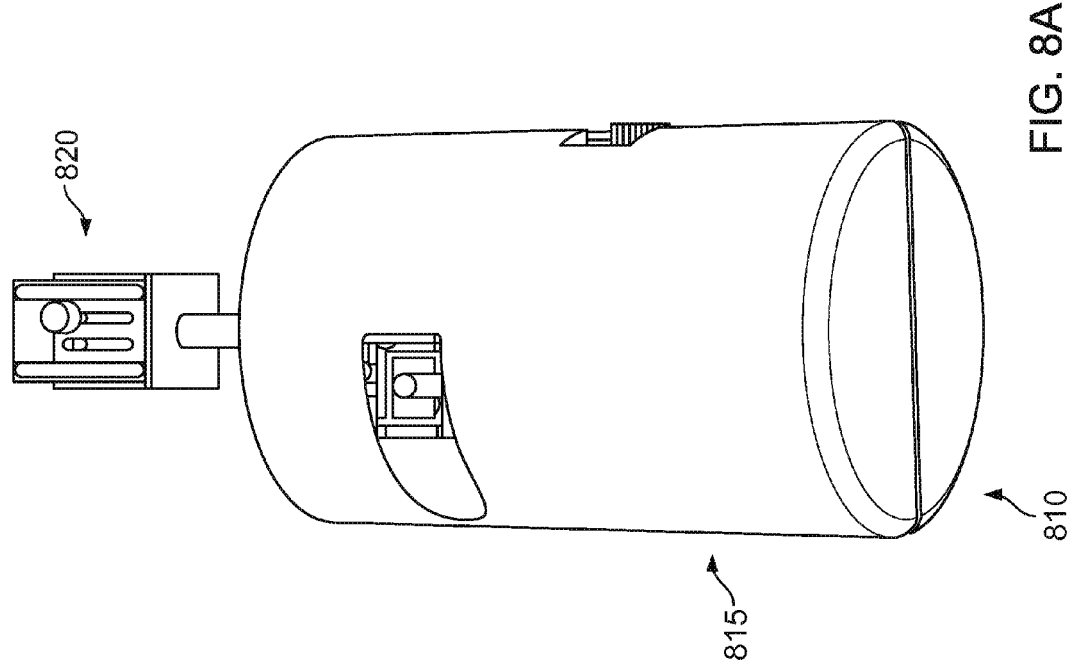
FIG. 8B
FIG. 8A

US 8,881,999 B2

FRAGRANCE DIFFUSION SYSTEM

CROSS-REFERENCE TO RELATED APPLICATIONS

This application claims priority to U.S. Provisional Application Ser. No. 61/366,027, filed on Jul. 20, 2010, the disclosure of which is incorporated by reference.

TECHNICAL FIELD

This disclosure relates to influencing airborne matter, and, more particularly, to introducing fragrant matter in an airspace.

BACKGROUND

Products can be developed to deliver scents or aromas in a commercial or office environment, such as in a retail environment. The scents can improve a customer's perception of the store, the environment and the products, and can make the customer want to revisit the store to buy something. Scents and systems can be customized to reflect and complement various brands, moods or environments.

SUMMARY

Generally, embodiments feature fragrance diffusion systems and methods. In some general aspects, a system for fragrancing air includes an adjustable fan that is used to generate an airflow to push a diffused fragrance in a particular direction from an output orifice of the system. The fragrance can be generated from atomized fragrance oil, where liquid fragrance oil is stored in a cartridge bottle assembly and then atomized using compressed air in a collector assembly in the system. When the system is mounted on a wall or ceiling, the adjustable fan can be used to direct the fragrance downward at any number of angles from the system. The system may be programmed to adjust a fan speed and various settings of the fragrance delivery.

The details of one or more implementations are set forth in the accompanying drawings and the description below. Other features will be apparent from the description and drawings, and from the example enumerated embodiments.

BRIEF DESCRIPTION OF THE DRAWINGS

FIG. 1A depicts an example of a top view of a fragrance diffusion system.

FIGS. 1B-1D depict examples of side views of the fragrance diffusion system.

FIG. 8A depicts an example of a view of the fragrance diffusion system with a ceiling mount.

FIG. 8B depicts an example of a view of the fragrance diffusion system with a wall mount.

Like reference numbers and designations in the various drawings can indicate like elements.

DETAILED DESCRIPTION

The details of various example embodiments are set forth in the accompanying drawings and the description below. In the following description, for the purposes of explanation, numerous specific details are set forth in order to provide a thorough understanding. It will be apparent, however, that the embodiments may be generally practiced without these specific details. Other features, objects, and aspects are apparent from the description and drawings.

Scent delivery systems can be developed to use atomization technology that releases a fragrance without sprays, or heated oils. The scent delivery systems can produce no messy residue to stain or damage floors or merchandise, so that scents can be delivered in a clean, controlled way. The scent delivery systems may require very little to no maintenance, other than adding or exchanging sealed fragrance cartridges for scents when the system is low or empty of liquids. The scent delivery system may be mounted onto a ceiling or a wall in locations where a person is likely to smell the fragrance, such as in a doorway, a hallway, behind or above a checkout counter, behind or above merchandise in a store, behind or above a receptionist's desk, a lobby room, or in a foyer, for example.

FIG. 1A depicts an example of a top view 110 of a fragrance diffusion system, and FIGS. 1B-1D depict examples of side views 120, 130, 140 of the fragrance diffusion system. The fragrance diffusion system can include an airblast venturi atomizing device that generally uses a high velocity air stream to break up a liquid from a cartridge bottle in the fragrance diffusion system into small particles which are small enough to "float" in the air (e.g., under 10 microns). The liquid inside of the cartridge bottle in the fragrance diffusion system can be a fragrant oil mixture. The high velocity air stream may be generated by an air pressure within the fragrance diffusion system that is greater than an air pressure outside of the device. In this regard, the fragrance diffusion system can be configured to maintain and deliver compressed air for the air stream. The atomized fragrance can be released into the airspace outside the fragrance diffusion system through the air stream. The movement of the atomized fragrance to the outside of the fragrance diffusion system can be assisted by air pushed from a fan to enhance the diffusion of the atomized fragrance in the airspace outside of the fragrance diffusion system and to provide a scented mist. The dimensions of the system, as shown in FIG. 1B, include a height of 9 inches, and a diameter across the bottom of 5.7 inches. The dimensions of the system are not limited to these dimensions, and can vary in other implementations.

Figure 2A:
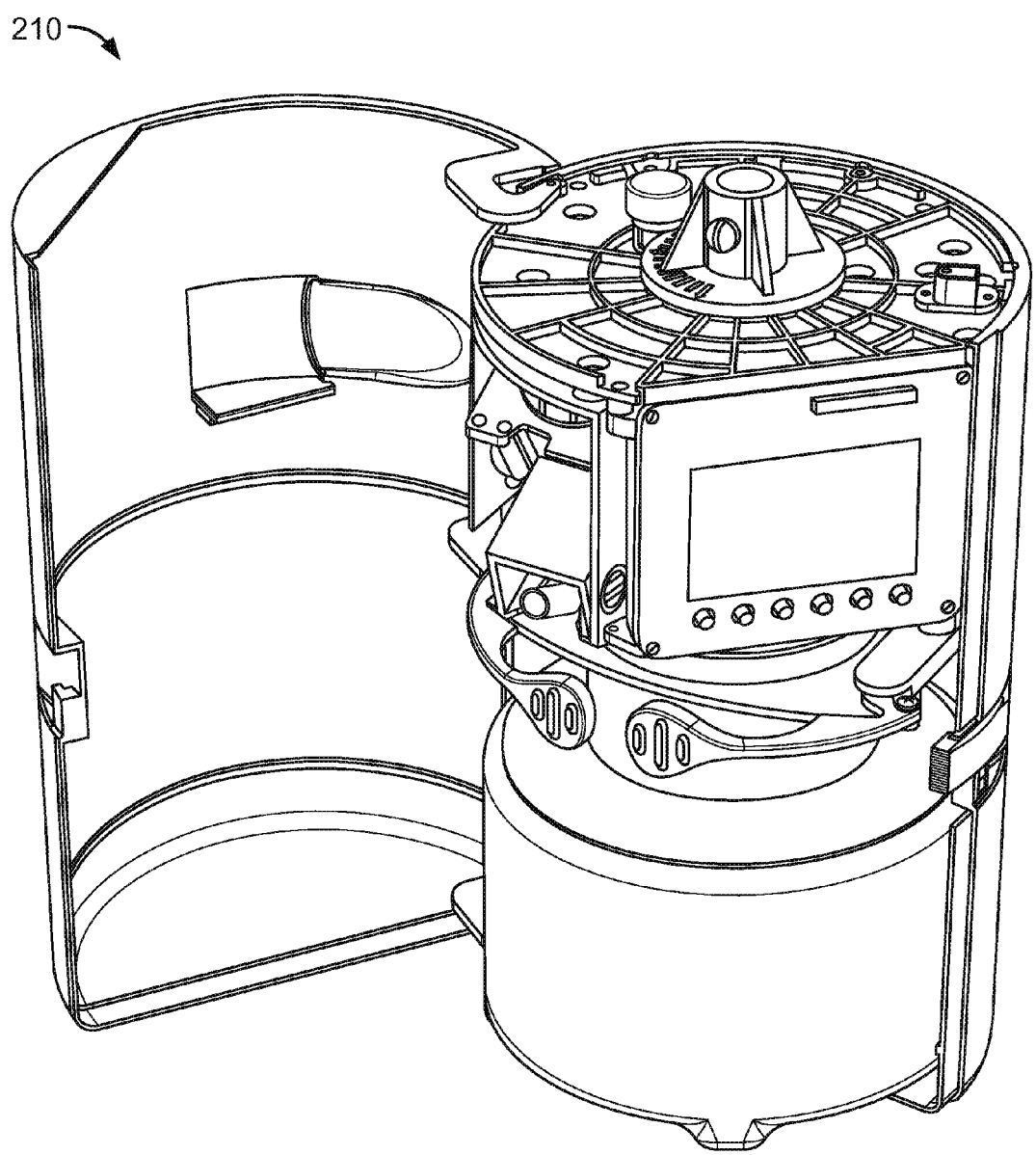
FIG. 2A depicts an example of a profile view of an interior of the fragrance diffusion system.
Figure 2B:
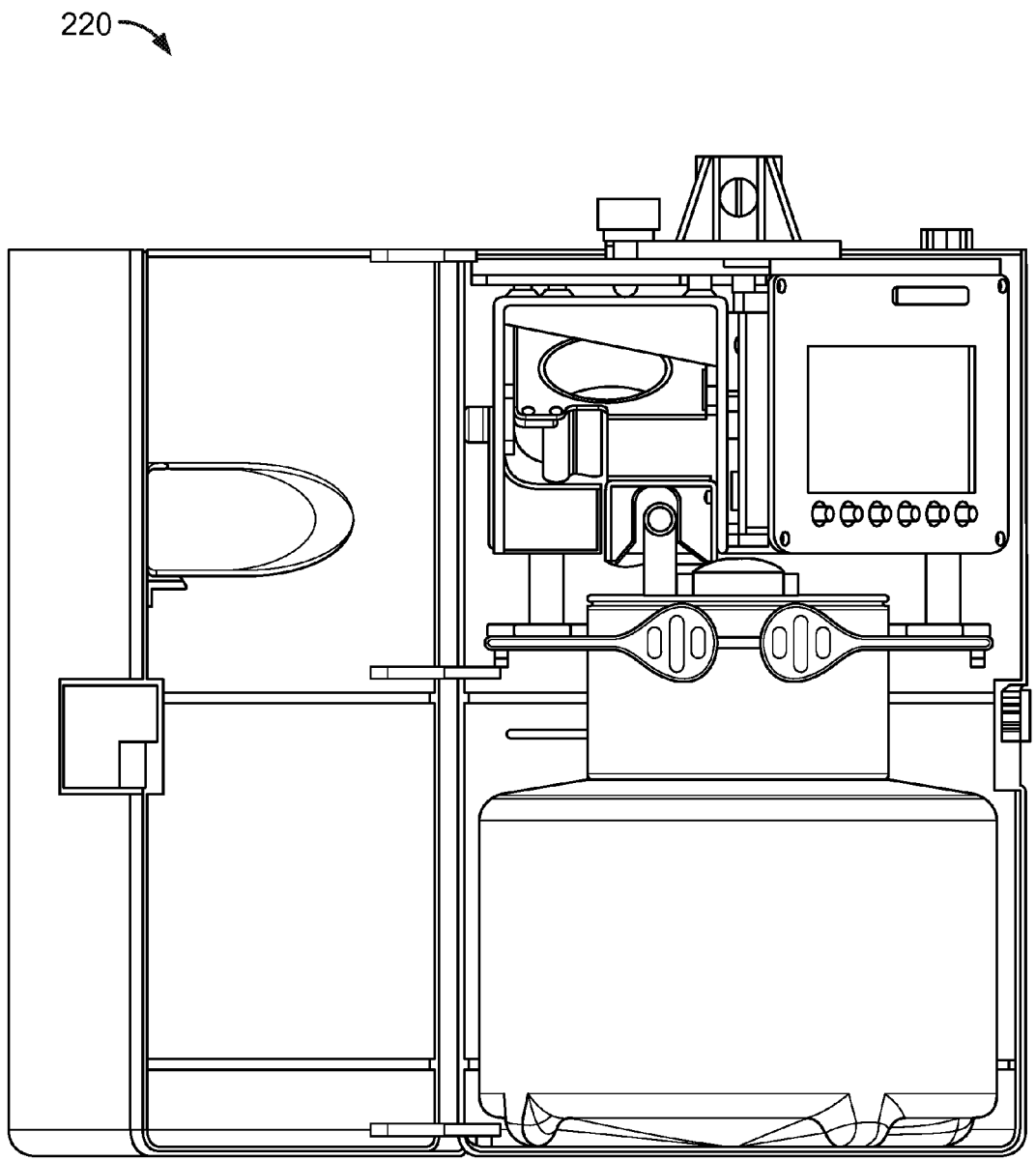
FIG. 2B depicts an example of a side view of the interior of the fragrance diffusion system.
Figure 3:
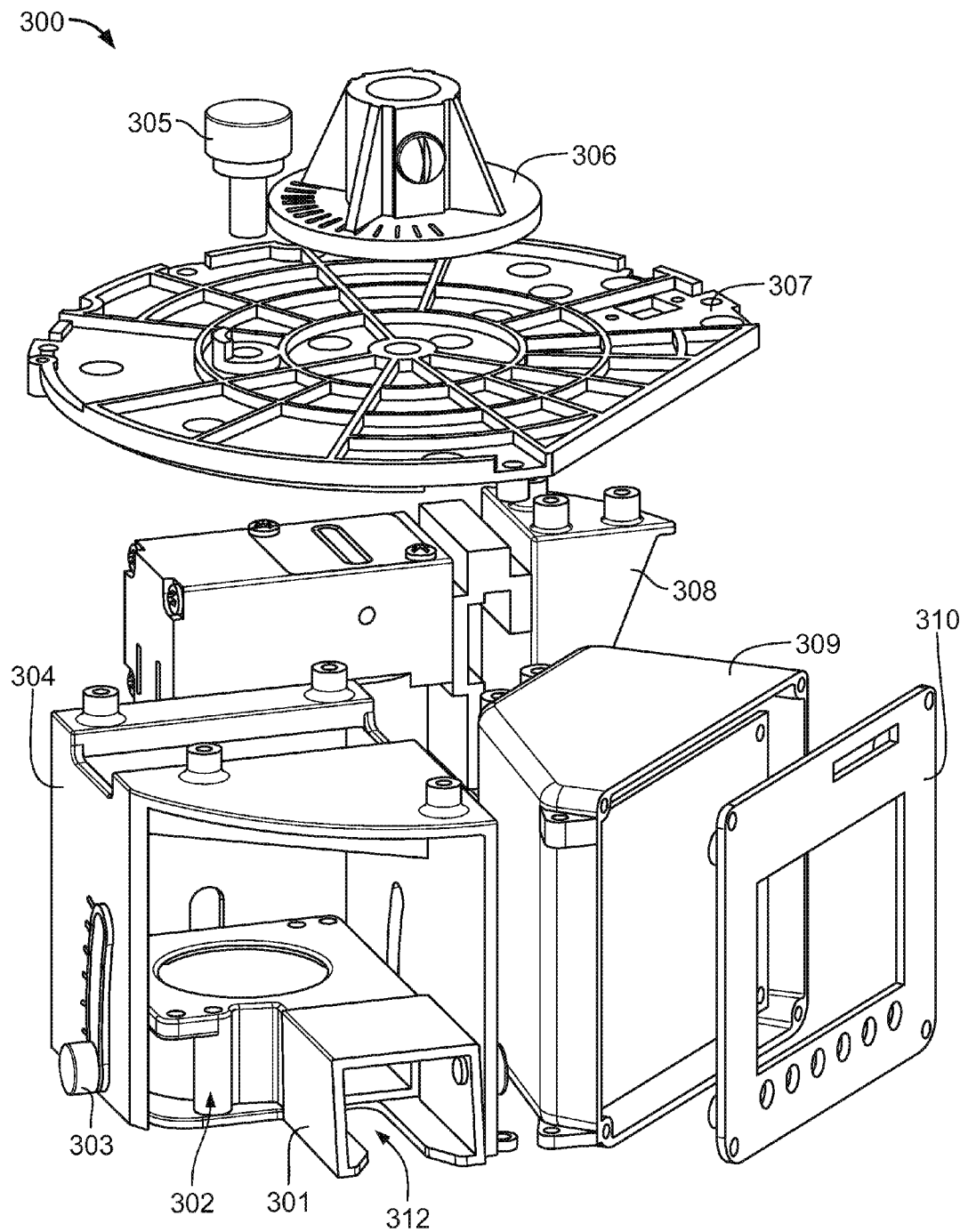
FIG. 3 depicts an example of interior components of the fragrance diffusion system.
Figure 4:
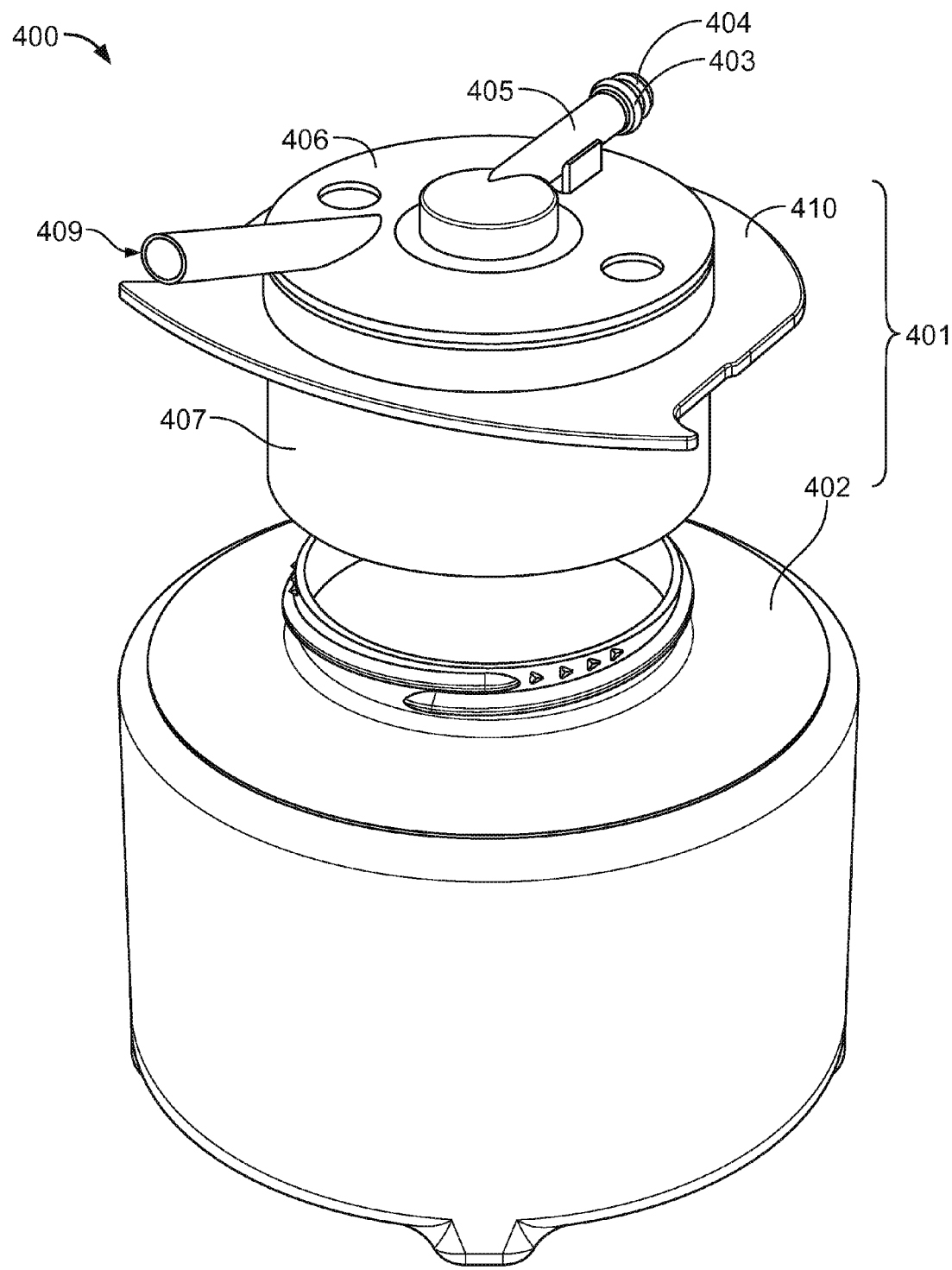
FIG. 4 depicts an example of a collector assembly and a cartridge assembly in the fragrance diffusion system.
Figure 5:
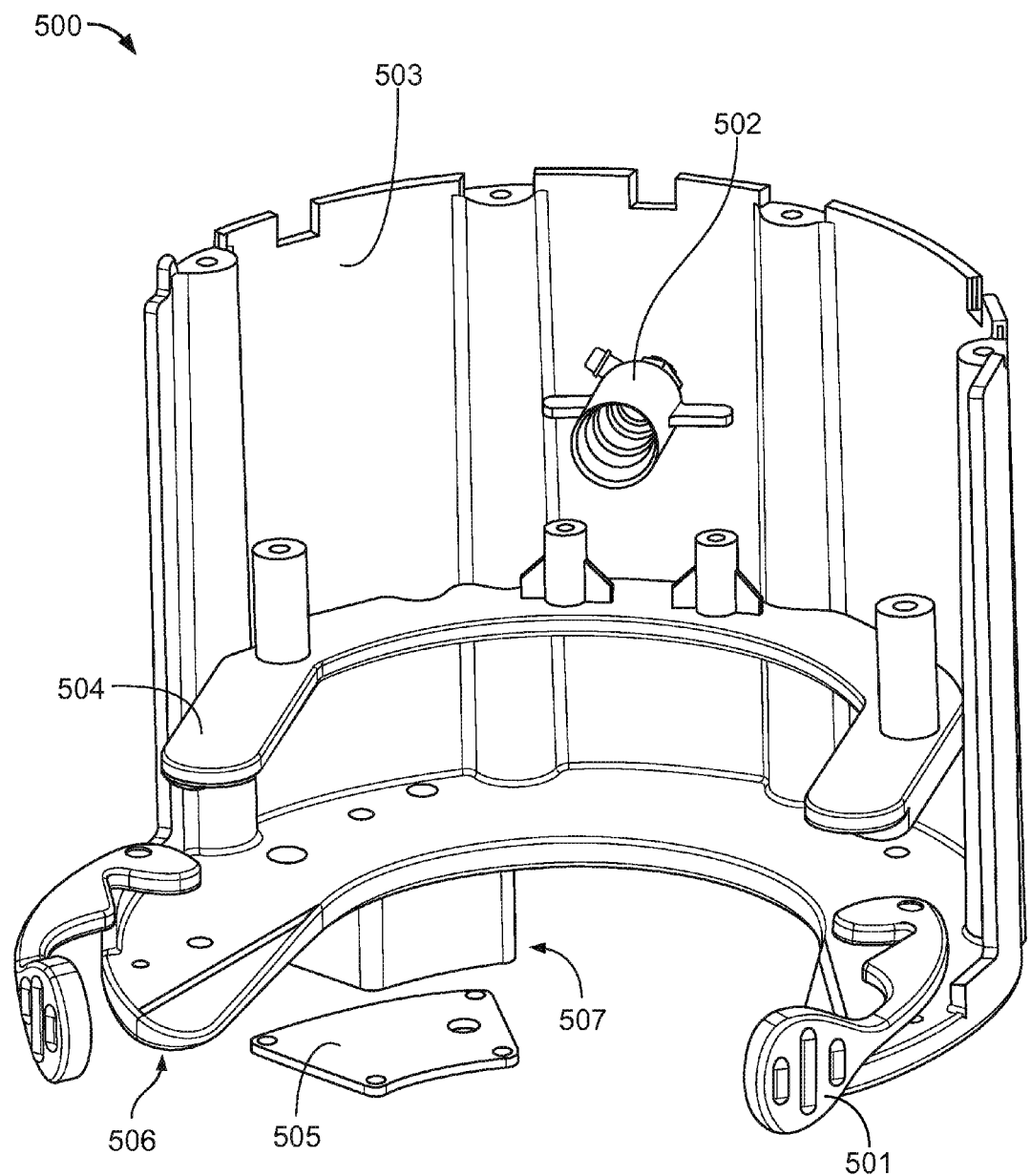
FIG. 5 depicts an example of a bottom chassis assembly in the fragrance diffusion system.

FIG. 2A depicts an example of a profile view 210 of an interior of the fragrance diffusion system, and FIG. 2B depicts an example of a side view 220 of the interior of the fragrance diffusion system. As described below, some of the interior components from the fragrance diffusion system shown in FIGS. 2A and 2B are shown in FIGS. 3-5. For instance, FIGS. 3-5 show diagrams of interior components of the fragrance diffusion system, where FIG. 3 depicts an example of interior components of a top chassis assembly 300, FIG. 4 depicts an example of some of the components related to a collector assembly 401 and a cartridge assembly 400, and FIG. 5 depicts an example of some of the components related to a bottom chassis assembly 500.

FIG. 3 shows the top chassis assembly 300 includes a rotating universal pivot bracket 306 for a mounting mechanism that serves as a horizontal adjustment for a particular fragrance direction by permitting the fragrance diffusion system to pivot up to 180 degrees. The rotating universal pivot bracket 306 mechanism also is configured for a quick disconnect of the apparatus from the mounting bracket for service. A lockable pivot bracket thumb screw 305 can be used to secure a targeted horizontal adjustment in a fixed position, where the pivot bracket thumb screw 305 can be tightened to lock the position of the targeted horizontal adjustment. The rotating universal pivot bracket 306 and the lockable pivot bracket thumb screw 305 can be attached to the top chassis 307, which is a circular-like plate that rests on top of a pump bracket 308, a fan bracket 304 and a printed circuit board (PCB) box 309. The pump bracket 308 is designed to hold an air pump (not shown) that works in the delivery of the compresses air inside the fragrance diffusion system. The pump bracket may also be use to shield the noise coming from the air pump. The fan bracket 304 is configured to hold a fan 302, and the PCB box 309 can be designed to hold circuit components and systems for controlling the operations of the system.

The fan 302 can be used to assist in the projection of the diffused fragrance vapor into the airspace outside of the system. In this system, the residual airflow from the compressed air output that is used to atomize the fragrance oil can be used to push out the diffused fragrance into the airspace, and the fan can be used to provide an additional air flow to push the fragrance across the airspace, thus delivering a more complete and consistent fragrance for a person to smell the fragrance. The fan assist feature also can eliminate the visual presence of a vapor cloud that is caused by the atomized fragrance as it departs the apparatus.

The fan 302 may have variable speeds to push the scent short or long distances from the system by increasing or decreasing the airflow and air speed of the fan 302. If the fragrance diffusion system is installed in a large area, for example, the fan speed can be adjusted to a high speed to push out the fragrance farther into the room. If the system is installed in a small area, such as in a small room, the fan speed may be adjusted to be at a lower speed since it may not take as much of an air flow to diffuse the fragrance into the smaller area. Depending on the type of fan 302 and the noise of the fan 302, the fan speed may be adjusted so that air flow can be provided in a space where the noise of the fan 302 is not noticeable to people in the room. In some implementations, for example, the fan 302 may be set at a fan speed that produces an air velocity of 370 ft/min. In some implementations, the fan 302 may be designed as a low-profile and compact design to fit inside the fan chassis 301, and may be designed to be a low-noise fan. In some implementations, the compact, low-profile design of the fan 302 can assist in enhancing the adjustability and maximum angle of the fan 302 in the fan bracket 304.

By providing the fan 302 in the system, in addition to the compressed air diffusing into the lower pressure airspace outside the system, the system can be mounted and placed into locations where it may not normally be placed when compared to using only an airflow resulting from a difference in pressure. The fan can also help the fragrance to be directed in a particular direction. The direction of the airflow from the fan 302 can also be adjusted by a lockable fan adjustment thumb screw 303. For instance, to allow for installation of the system at various heights by the user, the adjustable fan 302 can allow the user to adjust the air flow direction vertically for the best direction for the delivery of fragrance into the air space being scented. The fan 302 can be secured with a pivot point in the fan chassis 301 and can be adjusted up or down vertically with the use of the fan adjustment thumb screw 303 to tilt the fan in the preferred direction of the air flow. The fan adjustment thumb screw 303 can be tightened to fix the direction of the air flow. In some implementations, the fan 302 can be adjusted in a number of angles, such as anywhere from 0° to 30° downward, for example. The fan 302 can be adjusted in other angles in other implementations, such as by 45° downward or more from vertical for the system.

By having the fan 302 direction to be adjustable, the entire system does not have to be tilted to direct the fragrance in a particular direction. If the system was tilted, then there is a chance that the liquid oil would leak out of the system and onto the floor below. Also, a tilted system may not efficiently atomize the oil or provide an aesthetically-pleasing design. The location of the fan 302 in the system is at the output of the air exit at the fan chassis 301, and can be substantially flush with the outside front housing 710 of the fragrance system. The fan chassis 301 has a slot 312 located at a bottom area of the air exit to receive a fragrance from an output orifice 409 of the collector assembly 401 on the cartridge bottle assembly 400. The air pushed at the fan 302 can be air that has a lower pressure than the air coming from the output orifice 409. By having the slot 312 in the bottom on the fan chassis 301, the air flow from the fan can directly assist in pushing the fragrance away from the system. The fan chassis 301 can be used to channel the fragrance at the opening 750 of the outside front housing 710 of the fragrance diffusion system.

In other implementations (not shown), the fan 302 may remain stationary in the system, and the angle the output orifice 409 on the collector assembly 401 may be adjustable to change a direction of air flow from the system. In some other implementations, the fan chassis 301 can be adjusted independently of the fan 302 so that the fan chassis 301 may be enhance and/or channel the direction of the air flow.

The PCB box 309 has a PCB box face plate 310, which can be used to provide a mechanism for displaying and/or receiving information for controlling the operation of the fragrance diffusion system. The PCB box face plate 310 may have a glass, plastic, or transparent-like cover to display information regarding a status and controls for the operation of the fragrance diffusion system, and may be able to receive instructions from a user, or be configured with a slot or opening to receive a portable memory card (e.g., a flash memory card) that may contain operational data and/or system settings. The display may be presented, for example, in a liquid crystal display screen (LCD), in which some implementations may be able to have a touch-screen display to receive an input from a user. Some of the information that may be displayed, for example, may include an estimate of an amount of liquid oil left in the cartridge bottle, a time period for providing a short burst of fragrance into the air outside of the, and/or a programmable system for delivering the fragrance over an hourly, daily, weekly, monthly, or yearly schedule. For example, the controls for the fragrance diffusion system can be used for cycling the air pump that drives the atomizer on and off. In some implementations, for instance, the control settings can provide at least 50 different combinations of duty cycles and cycle lengths to better suit the desired average amount and timing of fragrance delivery into the air. The controls may also allow for at least 10 periods of fragrance delivery to be scheduled during a calendar week, for example. The occurrences of air delivery can be set as an "event" in the system, which can be associated with settings for the fragrance delivery, including both the duty cycle and the cycle length. The duty cycle can be the amount of time in the cycle length of fragrance delivery. The duty cycle and cycle length can be predetermined or adjusted by the user, for example, based upon the room or the environmental conditions for fragrance delivery. For example, an area with a large space may have a long time for airflow and/or a high speed for the fan to deliver the fragrance into the airspace at a greater rate than would be the case for a small room. The small area, for example, may have short time for airflow and/or a low speed for the fan to deliver the fragrance into the airspace.

Information serving as input into the system may be added by a user of the system, who can program settings using the interface in the PCB box 309, or the user can download instructions and settings onto the portable memory card and insert the memory card into the system. The user of the system may also refer to a service technician for the system.

The controls can allow for the fan speed to be varied, where the fan speed can be adjusted to be configured to the conditions of the airspace of the room and the noise generated from the fan. For example, a system that is mounted on a high ceiling may have controls configured such that the system has a high fan speed since the fragrance can be forcefully diffused into a large airspace without people noticing the noise generated from the fan. Whereas, the fan speed may be lower in a smaller and/or a quiet room.

Also, the controls can allow for the air pump to be adjusted so that different amounts of air pressure and resulting airflow can be utilized. For example, the air for the air pump can be adjusted to change a rate of diffusion of fragrance oil from the system, and or may be adjusted to allow for different physical characteristics of different fragrance oils to be used with the system. Some implementations of the system also may be able to have detector (not shown) to detect an amount of fragrance that is delivered into an airspace, and may be able to provide feedback to the system such that the airspace is not continuously saturated with the fragrance.

FIG. 4 depicts an example of a collector assembly 401 and a cartridge bottle assembly 400 in the fragrance diffusion system. The collector assembly 401 includes a nozzle 405, a collector top 406, the output orifice 409, a collector bottom 407, O-rings 403, 404 and a D-shaped guide plate alignment mechanism 410. The cartridge bottle assembly 400 includes the bottle 402 to hold the liquid fragrance oil. FIG. 5 depicts an example of a bottom chassis assembly 500 in the fragrance diffusion system. The bottom chassis assembly 500 includes a main chassis 503, an air adapter 502, a guide plate 504, a muffler assembly 507, a plenum cover 505, a cam lock mechanism 506, and two levers 501. The combination of the muffler assembly 507 and a plenum can be designed to reduce the noise from the air intake of the air pump by providing a restricted air input passageway.

The collector assembly 401 is formed with a D-shaped collector self alignment feature that allows the user to slide the collector assembly 401 into place where it aligns the collector assembly's nozzle 105 to the air adapter 502 located in the bottom main chassis 503. A D-shaped guide plate 504 in the bottom chassis assembly 500 can allow for a single orientation of the collector assembly 401 to the guide plate 504. In some implementations, the guide plate 410 may have some other shape than a D-shape. Dual-levers 501 for the cam lock mechanism 506 may provide for a convenient one-hand insertion and lock of the fragrance cartridge bottle assembly 400. The cam lock mechanism 506 also can provide a convenient one-hand unlock and cartridge removal action that may not require any tools for the unlocking and/or the removal.

The fragrance diffusion system can use a replaceable cartridge bottle assembly 400 with the output orifice 409 attached to the collector top 406. The output orifice 409 can be aligned such that when the collector assembly 401 is self aligned upon insertion by the D-shaped guide plate alignment mechanism 410, the output orifice 409 can be configured such that the fragrance output is centered on the slot 312 at the air flow from the fan chassis assembly 301, which can result in an evenly-distributed fragrance as it leaves the housing assembly 700. The fragrance diffusion system includes the intake muffler assembly 507 that can serve as an input air filter and a noise muffler. The dimensional characteristics of the muffler chamber can act to suppress the air intake noise from the air pump. The muffler assembly 507 can have one or more unique chambers that cancel most of the noise generated by the air intake of the air pump.

The system includes a seal feature for multiple o-rings 403, 404 on the compressed air input to the collector assembly's nozzle 405 to help overcome a corrosive nature of most fragrance oils. For example, some fragrance oils can break down plastics over time, and the reliability of the collector assembly 401 can be reduced if the o-rings 403, 404 and/or the nozzle 405 becomes wet with the liquid fragrance oil. In this implementation, the fittings for the multiple o-rings 403, 404 can be designed to be progressively larger in size to create multiple levels of isolation from the fragrance oil and to enhance the reliability of the seals. The o-rings 403, 404 are part of the replaceable collector assembly 401 so that each time the collector assembly 401 (or cartridge bottle assembly 400) is replaced a new set of o-rings 403, 404 can be used. Service problems resulting from defective o-rings can be reduced by designing the system such that the o-rings are included as part of the replaceable cartridge. A stainless steel air adapter 502 attached to the guide plate 504 can help ensure that the system is not damaged by the corrosiveness of the fragrance oil.

Some implementations may have a cap (not shown) to cover the opening of the nozzle 405 during for use during shipping. The cap may be able to withstand a force of the fragrance oil moving in transit while keeping the o-rings 403, 404 free from the corrosive fragrance oil. A threaded cap with plug can be designed to keep the oil away from the o-rings 403, 404. This treaded cap and plug can enhance the shelf life of the o-rings and reducing and/or eliminating air leaks during use as a result of having one of the o-rings being damaged by the fragrance oil.

To prepare the collector assembly 400 for shipping, the output orifice 409 may not be installed during shipping, but can be installed when the system is ready for use. The output orifice 409 may be detachable, and may be installed at an angle with respect to the collector top 406. The angle of the output orifice 409 can generally be at any angle, so as long as the output orifice 409 directs the air flow in a proper direction out of the system. During shipping, a plug may be inserted in the collector assembly 401 when the output orifice 409 is removed to prevent any damage from any movement or liquid fragrance oil. In some implementations, the angle of the output orifice 409 may be 45° with respect to the collector top 406, for example. The output orifice 409 can be designed such that it is not too short for the fragrance to be diffused from the system. The output orifice 409 may not also be too long so that the diffused fragrance would not be close enough to mix with the air from the fan's output.

Figure 6A:
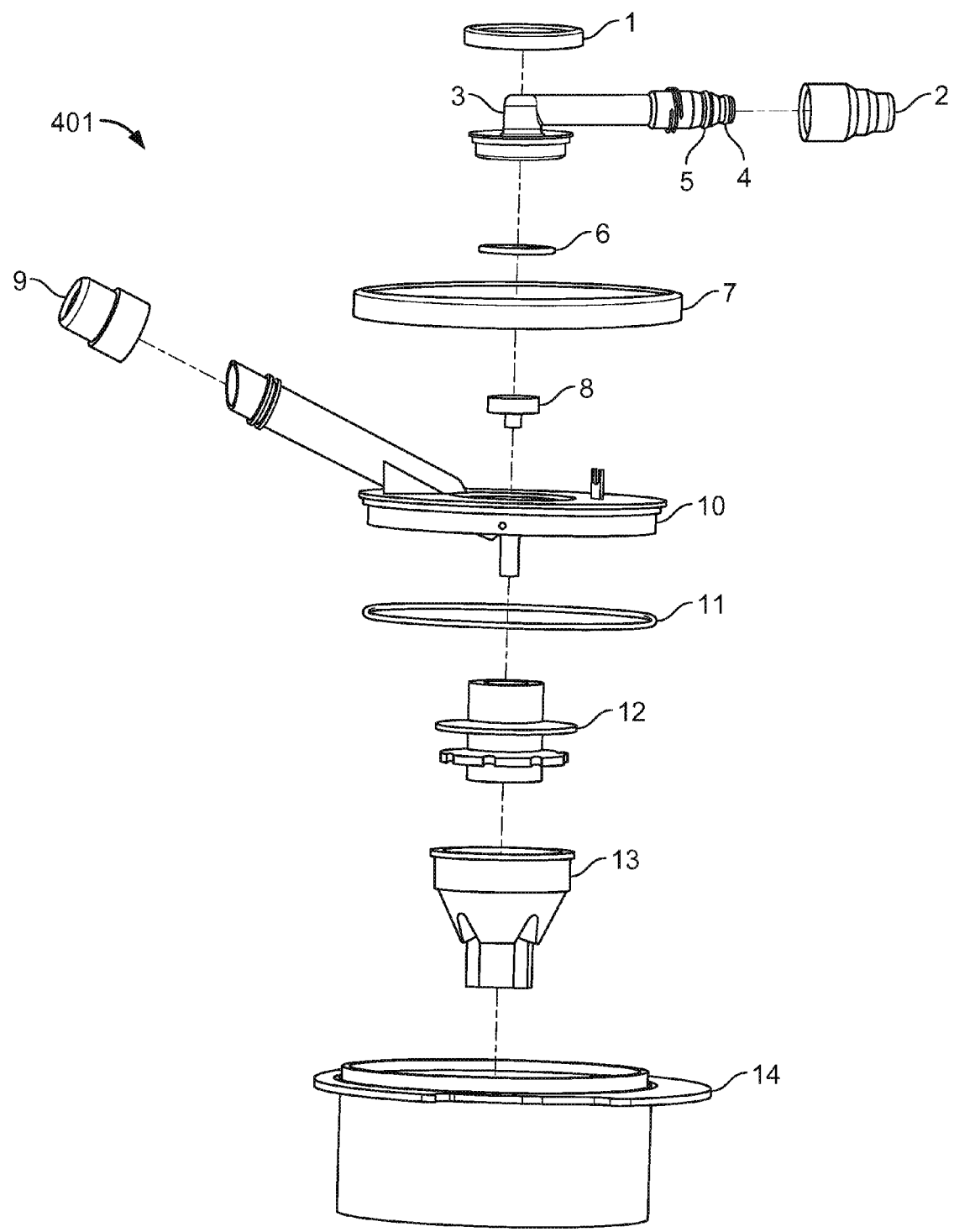
FIGS. 6A-6F depict examples of various views related to the collector assembly.
Figure 6B:
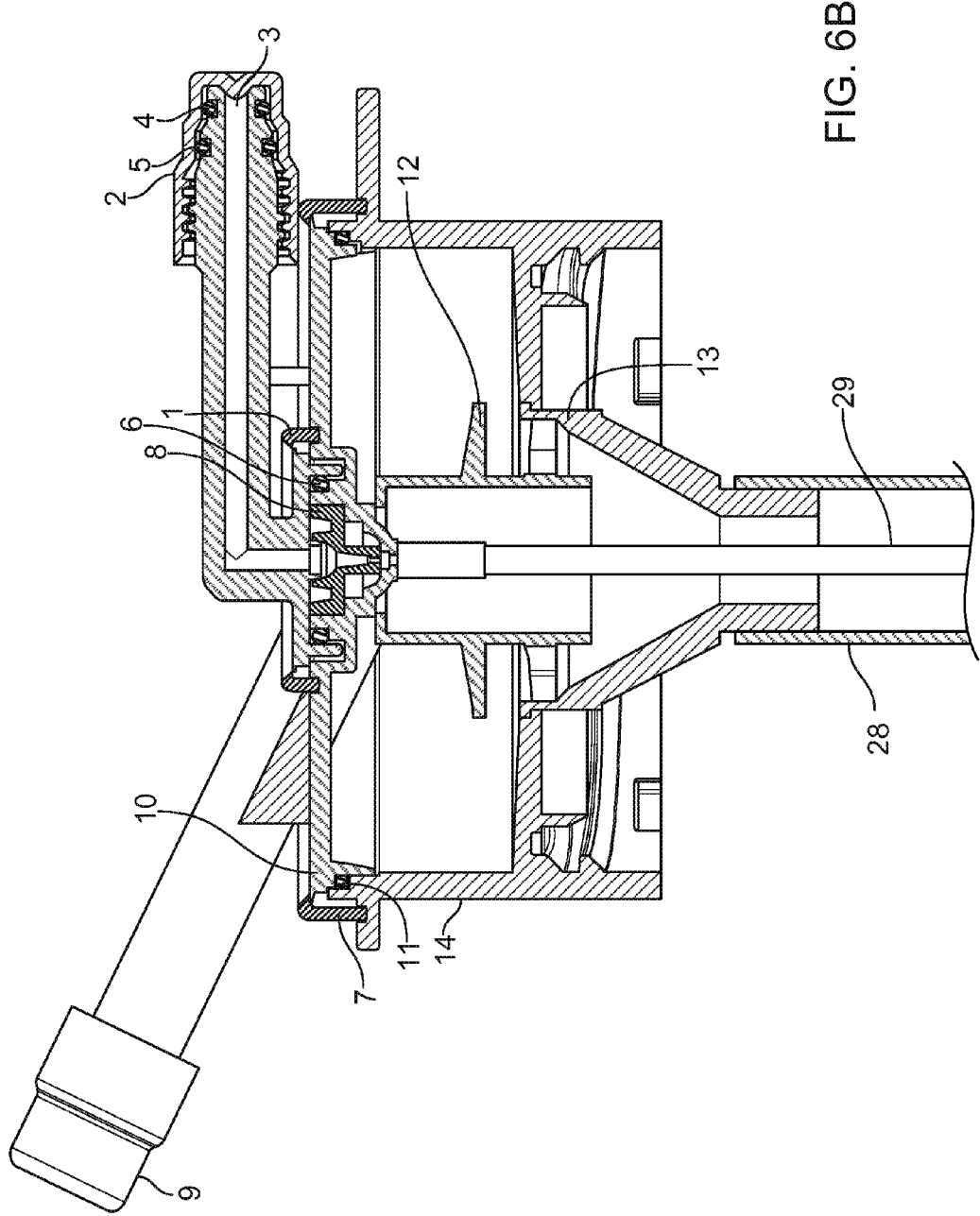
Figure 6C:
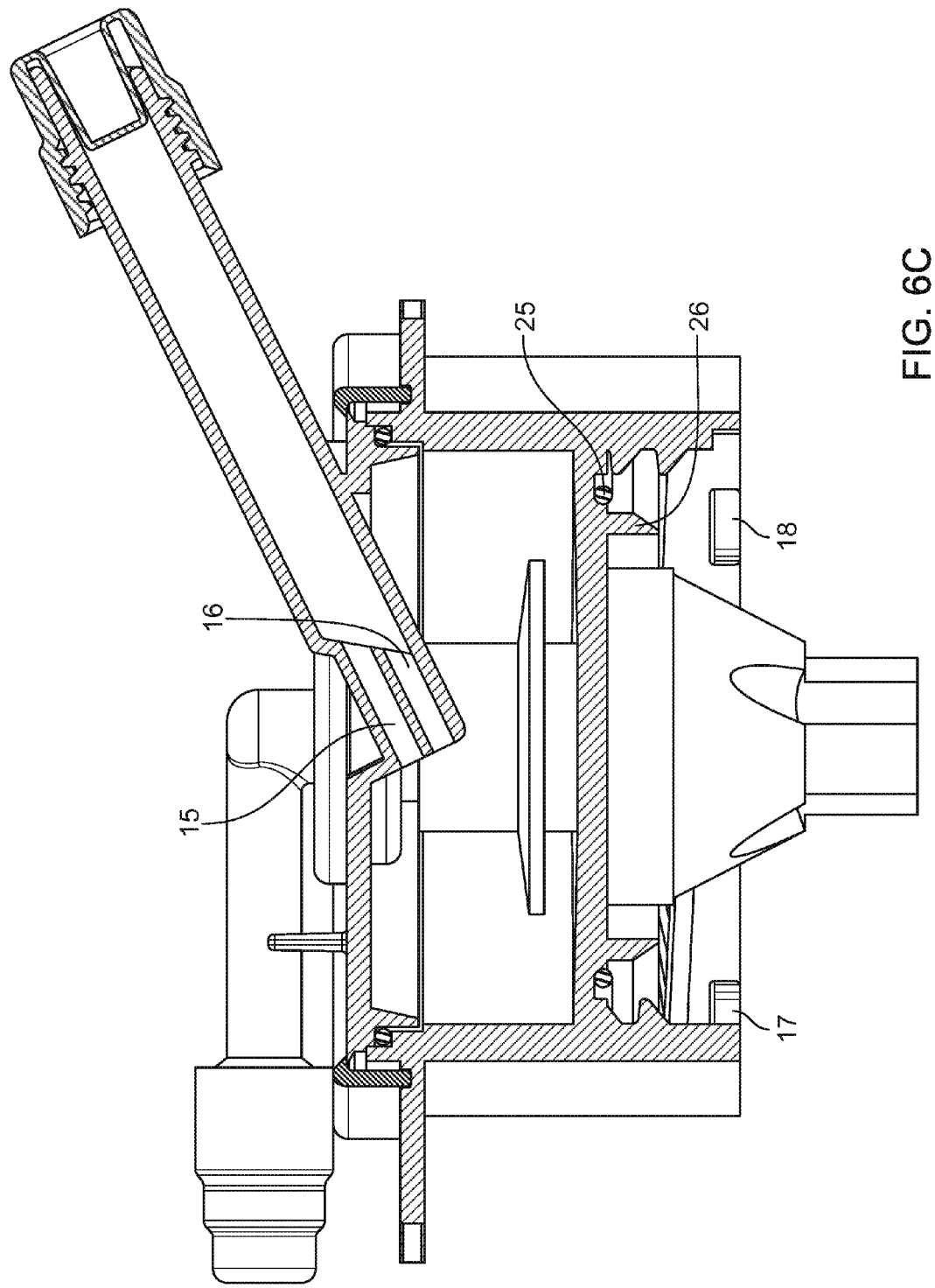
Figure 6D:
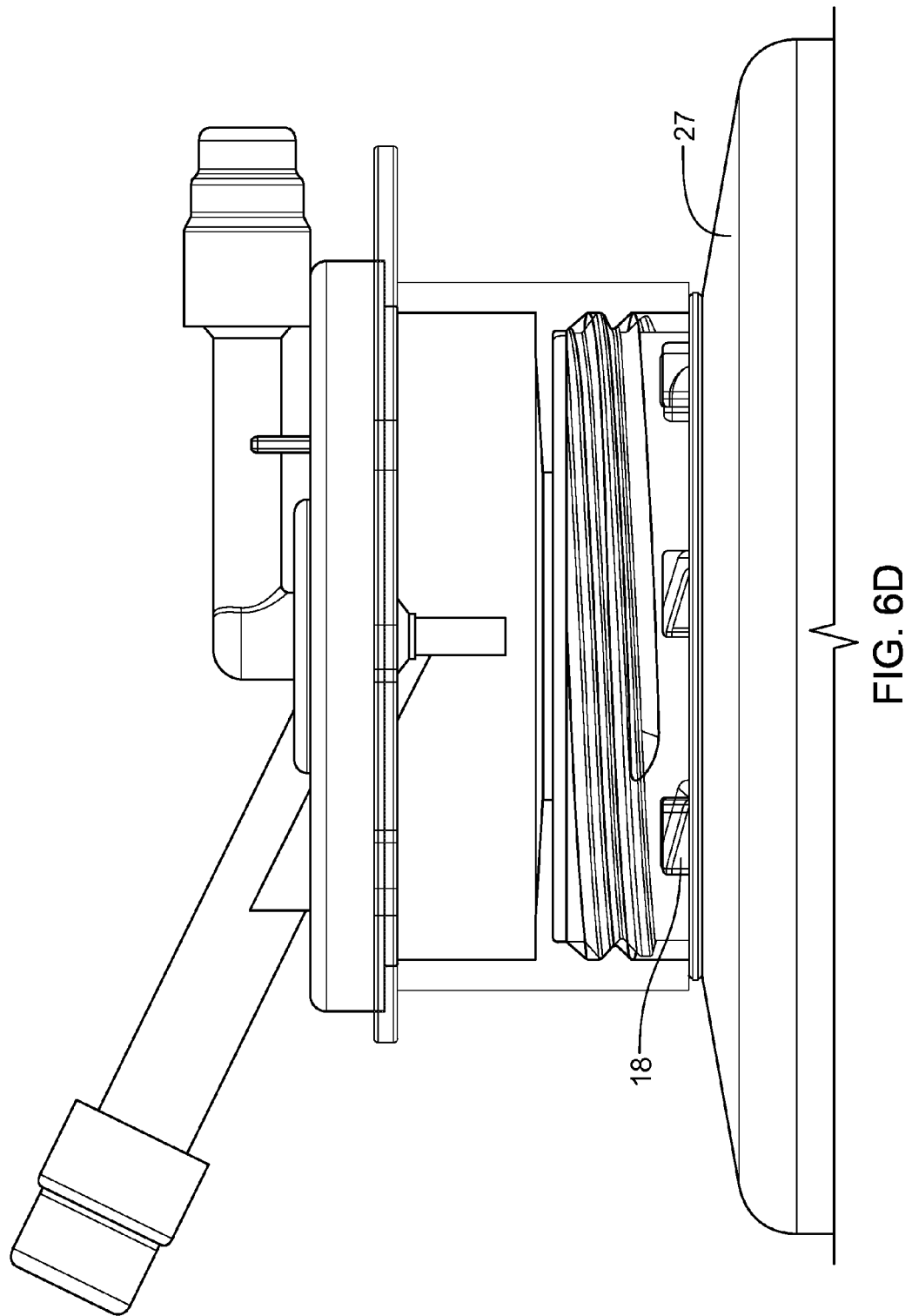
Figure 6E:
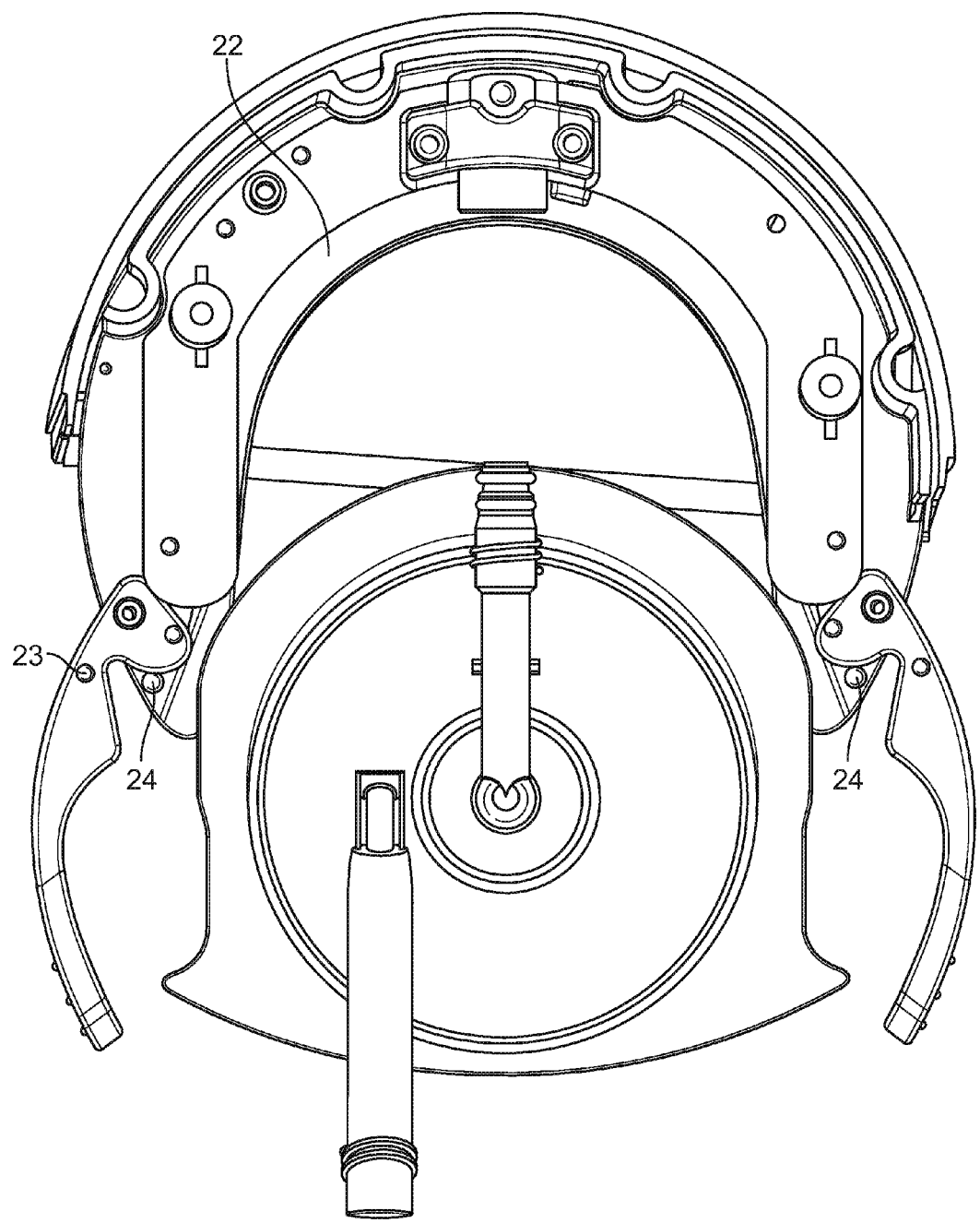
Figure 6F:
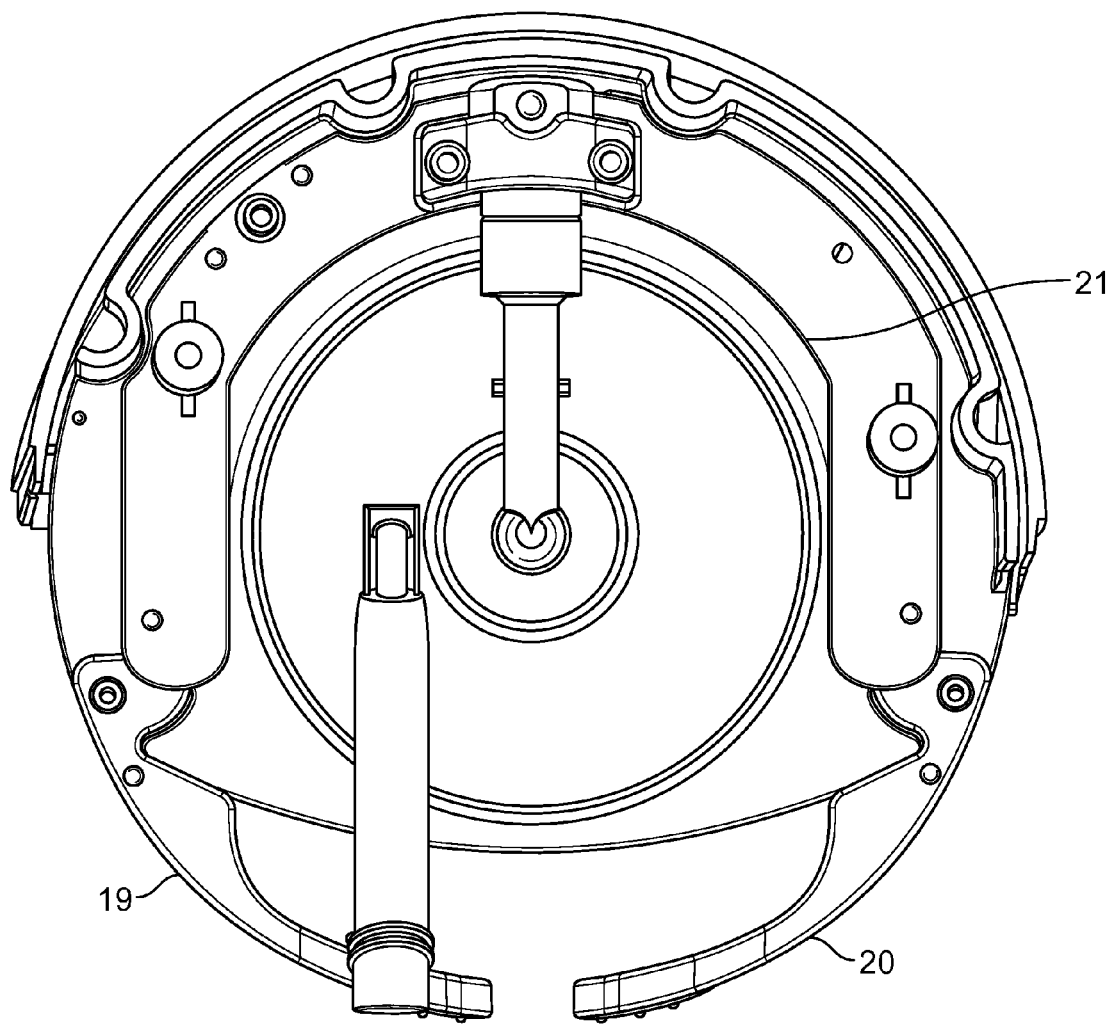
Figure 7:
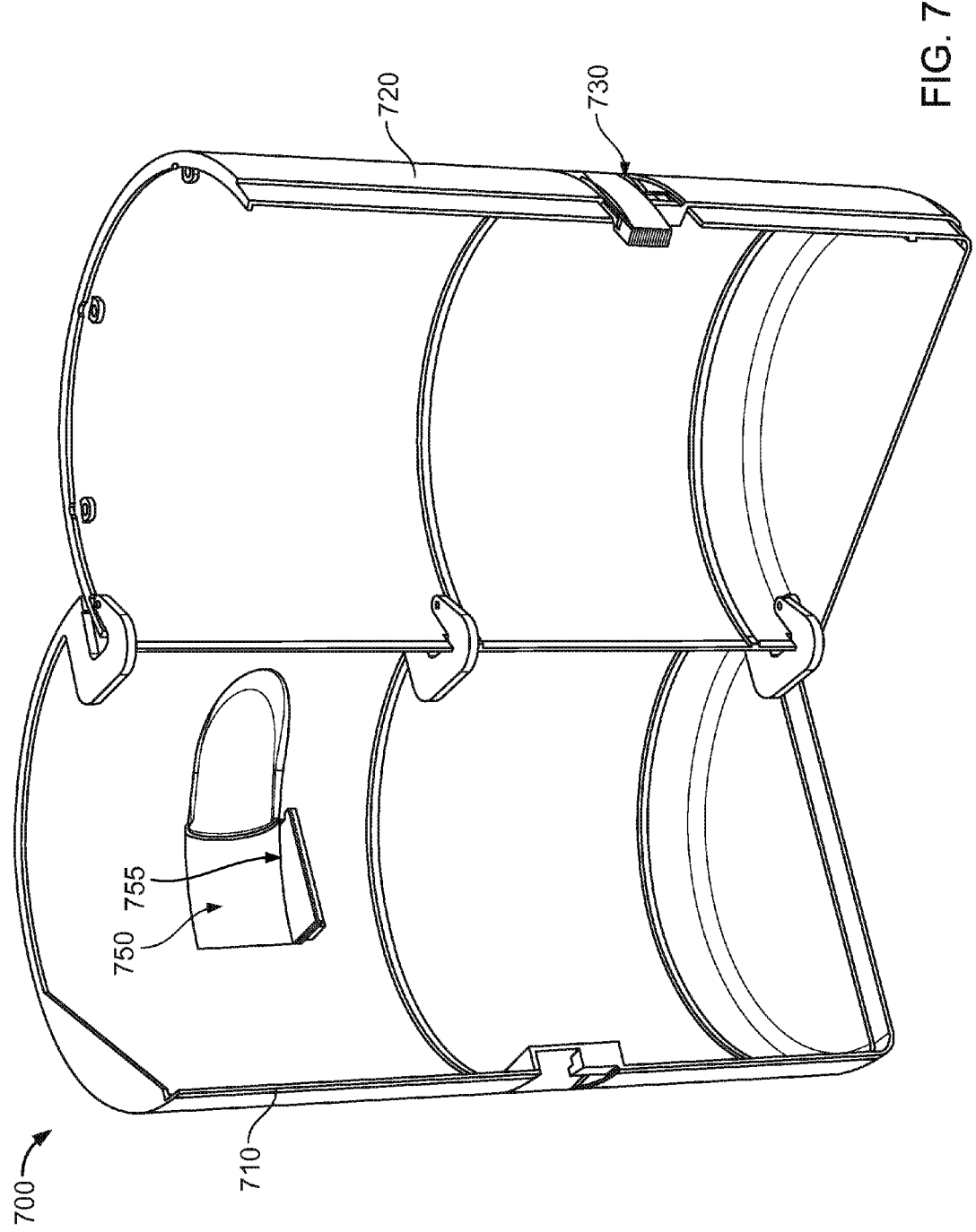
FIG. 7 depicts an example of a housing assembly in the fragrance diffusion system.

Some implementations of the fragrance diffusion system can involve generating a scented mist of atomized liquid fragrance oil. The system may include an atomizer complex in the collector assembly 401 to the atomize liquid fragrance oil into scented particles and deliver the scented particles to air outside of the atomizer complex, where the scented particles that are not delivered to the air outside of the atomizer complex are coalesced and returned to the bottle 402. The nozzle 405 can be configured to receive the compressed air from the air pump. The device can include a drainage tube 28 (FIG. 6B) extending from a bottom area of the atomizer complex into the liquid fragrance oil, where the drainage tube 28 can include a vacuum tube 29 (FIG. 6B) inside of the drainage tube 28 (or outside and parallel to the drainage tube) that extends along a longitudinal length down the drainage tube 28. The drainage tube 28 can be configured to at least contact a level of the liquid fragrance oil in the bottle 402. The drainage tube 28 can be configured so that the collected oil from the atomizer complex drains down the drainage tube 28 into the liquid fragrance oil in the cartridge bottle assembly 400. The device can be configured to filter the liquid fragrance oil in the cartridge bottle assembly 400 and the collected oil from the atomizer complex that drained down the drainage tube 28. The vacuum tube 29 can be configured to suction the filtered liquid fragrance oil and/or the collected oil in the bottle 402 into the atomizer complex for atomization. Except for the atomized liquid fragrance oil that is delivered into the air as the scented fragrance, the device can be configured to constantly recirculate the oil in the device so that the oil remaining in the device is constantly filtered.

FIGS. 6A-6F depict examples of various views related to the collector assembly. FIG. 6A shows various parts of the collector assembly, and where those parts fit into the collector assembly. The parts includes a snap ring 1, an input cap 2, an input tube 3, o-rings 4, 5, 6, 11 a snap ring 7, a nozzle 8, an output cap 9, a collector top 10, a collector center 12, a funnel 13, and a collector bottom 14. In assembling the collector assembly 401, the snap ring 1 can be sonically welded to the collector top 10 and can hold the input tube 3 against the rubber o-ring 6 while creating a seal without a gasket to the nozzle 8. The input tube 3 can be used to form a non-gasket seal with the nozzle 8 that is positioned between two conical surfaces. O-rings 4, 5 can be used to form a double seal by forming a seal to the cap 2 and a seal to the compressed air input. Another o-ring 6 can form a radial seal against the collector top 10 in order to maintain a low pressure vacuum in between the collector bottom 10 and the nozzle 8. Another snap ring 7 can be sonically welded to the collector top 10, which can be configured to hold the collector top 10 to the collector bottom 14. In some implementations, the collector top 10 can be held to the collector bottom 14 by utilizing multiple locking tabs located on the snap ring 7 with matching slots located on collector bottom 14.

The nozzle 8 can be pressed against the collector top 10 via the input tube 3 to create a seal without a gasket between the two conical surfaces, and to align an exit for the nozzle 8 with the output orifice 409 on the collector top 10. The output cap 9 can prevent an oil spill while the collector assembly 401 is being stored and shipped, for example. The input cap 2 can be configured to screw onto the input tube 3 and create a seal with a dimple on the input cap 2 and the air line in the input tube 3. The seal created by the input cap 2 on the input tube 3 can be useful, for example, during storage and shipping to prevent an oil spill. The collector top 10 can have a molded output tube and can be attached to the input tube 3. A seal can be created between the collector top 10 and the collector bottom 14 via the o-ring 11, for which the seal can prevent low pressure fragranced air from exiting the input tube 3 anywhere except at the output tube on the collector top 10. The collector center 12 can be pressed to fit into the funnel 13 via the collector top 10, and can be used to aid in separating the larger particles from the smaller particles. The funnel 13 can sit in the collector bottom 14 and can act to capture large particles and prevent the large particles from leaving the collector assembly 401. The collector bottom 14 may form a main part of the body of the collector assembly 401, and the collector bottom 14 can be the part of the collector assembly where the fragranced air is collected before the fragranced air exits from the output tube.

FIGS. 6B-6D show various parts of the collector assembly, and where those parts fit into the collector assembly. FIGS. 6C and 6D also show, for example, an o-ring 25, a rib 26 on the bottom of the collector bottom 14, a bottle 27, holes 15, 16 in the output of the collector top 10, and notches 17, 18. The o-ring 25 can service as a secondary seal for the bottle 27. The rib 26 on the bottom of collector bottom 14 can create an interference seal between collector bottom 14 and the bottle 27. Holes 15, 16 can be located at the bottom of the output tube and stacked vertically above one another. The holes 15, 16 can have a certain length and diameter so as to lower a sound volume that exits the collector assembly due to the exiting atomized fragrance oil. The holes 15, 16 can also be configured to control the particle size, as well as to allow any collection of oil in the output tube in the collector top 10 to drain back into collector assembly. The notches 17, 18 can be two of six such notches, for example, that may correspond with six matching extrusions on the bottle, which can serve to lock the bottle 27 and the collector assembly in the correct position, as well as serving to provide tamper protection for the collector assembly and the bottle from unauthorized users.

FIGS. 6E and 6F show the collector assembly with a D-shaped collector self alignment feature 21 that allows the user to slide the collector assembly into place. A D-shaped guide plate 22 in the bottom chassis assembly can allow for a single orientation of the collector assembly to the guide plate. The collector assembly can be held into place by levers 19, 20, which can lock into place when closed to hold the collector assembly tight against the air pressure from the apparatus by using (locking) tabs 23, 24 on each side.

FIG. 7 depicts an example of a housing assembly 700 in the fragrance diffusion system. The housing assembly 700 has a first part for a front housing 710, and a second part for a back housing 720, and a slide lock 730 to lock the front and back housings 710, 720 together around the inner components of the fragrance delivery system. The front and back housings 710, 720 can open in a manner such that most of the interior components of the system can be made available and serviceable to a service person for the system, the cartridge bottle assembly 400 can be inserted into and removed from the system, and the user can program and control the system using the interface on the accessible PCB box 309.

The front housing 710 has an opening 750 to receive the fan chassis 301 and output orifice 409. The opening 750 has a shelf 755 that can include an absorbent material (not shown) that can collect any condensed fragrance oil from the output of the system. The collected, condensed fragrance oil on the absorbent area of the shelf 755 may be evaporated by the air from fan 302 and sent out of the opening 750. The location of the opening 750 is not limited to the implementation shown in the drawings, but can be made generally near anywhere in the front and back housings 710, 720.

FIG. 8A depicts an example of a view 810 of the fragrance diffusion system 815 with a ceiling mount 820. In some implementations, the ceiling mount 820 may be a universal track mount, which can fit to any number of track types and sizes. FIG. 8B depicts an example of a view 810 of the fragrance diffusion system 815 with a wall mount 840.

In some implementations, the bottle 402 may be designed such that the fragrance oil in the bottle 402 may not be refillable by a user, but the bottle 402 may have to be ordered and replaced by a manufacturer or distributor of the bottle with a supply of liquid fragrance oil inside of the bottle 402.

Some of the described embodiments of the subject matter and the operations can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal, which is generated to encode information for transmission to suitable receiver apparatus for execution by a data processing apparatus. The data processing apparatus may include the sensor, may be part of the sensor, may be a part of a system with the sensor, may be integrated within the system and/or sensor, may be part of receivers, transmitters, components and/or logic associated with the sensor or the receivers and/or transmitters, or any combination thereof. A computer storage medium can be, or be included in, a computer-readable storage device, a computer-readable storage substrate, a random or serial access memory array or device, or a combination of one or more of them. Moreover, while a computer storage medium itself is not a propagated signal, a computer storage medium can be a source or destination of computer program instructions encoded in an artificially generated propagated signal. The computer storage medium can also be, or be included in, one or more separate physical components or media (e.g., other storage devices). Some of the operations described in this specification can be implemented as operations performed by a data processing apparatus on data stored on one or more computer-readable storage devices or received from other sources.

Various apparatuses, devices, and machines for processing data, may be used as a "data processing apparatus," including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and an input device, such as a pointing device, a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be useful.

Although only a few embodiments have been described in detail above, other embodiments are possible. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be excised from the combination, and the combination may be directed to a subcombination or variation of a subcombination. It should be appreciated that disclosed embodiments may encompass equivalents and substitutes for one or more of the example techniques described herein. The present specification describes specific examples to accomplish a more general goal in another way. This description should be understood to represent example embodiments and the following are intended to cover any equivalent, modification or alternative. Accordingly, other implementations are within the scope of the following example enumerated embodiments and claims.

Although the present invention is described above and defined in the attached claims, it should be understood that the present invention can alternatively also be defined in accordance with the following embodiments:

LISTING OF SOME EXAMPLE ENUMERATED EMBODIMENTS

1. A system for fragrancing an air space comprising:
a cartridge assembly;
a collector assembly, comprising:
   a nozzle to receive compressed air;
   a collector bottom to receive liquid fragrance oil from the cartridge assembly; and
   an output orifice,
wherein the collector assembly is configured to atomize the liquid fragrance oil from the cartridge assembly and diffuse a fragrance from the collector assembly through the output orifice,
wherein the cartridge assembly is configured to hold the liquid fragrance oil, wherein the cartridge assembly is configured to interface with the collector assembly so that the liquid fragrance oil is drawn up into the collector bottom; and
a top chassis assembly comprising an adjustable fan, wherein the adjustable fan is configured to interact with the diffused fragrance from the output orifice to force the diffused fragrance away from the system.

2. The system of example enumerated embodiment 1, further comprising a fan adjustment mechanism to fix the adjustable fan in a direction at a downward angle in the system.

3. The system of example enumerated embodiment 2, wherein the adjustable fan comprises an on opening for an output of a fan-forced airflow, wherein the system comprises a fan chassis at the output of the adjustable fan, wherein the fan chassis is configured to channel the fan-forced airflow at the output of the adjustable fan.

4. The system of example enumerated embodiment 3, wherein:
the fan chassis comprises a slot, wherein the slot in the fan chassis is configured to receive the output orifice from the collector assembly.

5. The system of example enumerated embodiment 4, further comprising:
a front housing with a front side, a backside, and an opening configured for receiving the fan chassis and the output orifice;
a back housing with a front side and a backside;
a hinge to connect the front and back housings at the backside of each of the front and back housings, wherein the front and back housings are configured to enclose the collector assembly, the cartridge assembly, and the top chassis assembly; and
a locking mechanism on the front side of the front and back housings to lock the front and back housings at the front side upon closing the front and back housings.

6. The system of example enumerated embodiment 5, wherein the top chassis assembly comprises an interface to display a status of the system or to receive user input for system settings or instructions.

7. The system of example enumerated embodiment 6, wherein the system further comprises a bottom chassis assembly that is configured to receive the collector assembly and the cartridge assembly, wherein the bottom chassis assembly comprises:
a guide plate for receiving the collector assembly; and
a locking mechanism for securing the collector assembly in the bottom chassis assembly,
wherein the collector assembly comprises a guide plate that is configured to interface with the guide plate of the bottom chassis assembly so that the collector assembly is configured to be received into the bottom chassis in a predetermined direction.

8. The system of example enumerated embodiment 7, wherein the bottom chassis assembly comprises a muffler assembly that is configured to serve as an air filter and a noise muffler for the system.

9. The system of example enumerated embodiment 7, wherein the adjustable fan is configured to tilt at an angle from 0° to 30° downward from the system.

10. The system of example enumerated embodiment 9, wherein the interface comprises a printed circuit board with components configured to receive and process the instructions for operations of the system, wherein the instructions comprise a setting of a fan speed, a setting of a compressed air flow, or a schedule for delivering the fragrance outside the system, wherein the schedule comprises a duty cycle and a cycle length of the duty cycle.

11. The system of example enumerated embodiment 10, wherein the nozzle comprises at least two o-rings, wherein the at least two o-rings differ in a size.

12. The system of example enumerated embodiment 11, wherein the output orifice is configured to be detachable from the collector assembly, and wherein the output orifice is configured to be attachable at an angle to the collector assembly.

13. The system according to one of the preceding embodiments, characterized in that the system is configured to be programmed to adjust a fan speed and various settings of the fragrance delivery.

14. The system according to one of the preceding embodiments, characterized in that the top chassis assembly further comprises:
a universal pivot bracket;
a lockable pivot bracket thumb screw;
a pump bracket; and
a fan bracket.

15. The system according to embodiment 14, characterized in that the pump bracket is designed to shield noise coming from an air pump.

16. The system according to one of the preceding embodiments, characterized in that the fan has variable speeds.

17. The system according to one of the preceding embodiments, characterized in that the fan can be adjusted in an angle from 0° to 45° downward or more from the system.

18. The system according to one of the embodiments 3 to 17, characterized in that the fan chassis is adjustable independently of the fan.

19. The system according to one of the embodiments 6 to 18, characterized in that the printed circuit board comprises a face plate for displaying information of a programmable system for delivering the fragrance over an hourly, daily, weekly, monthly or yearly schedule.

20. The system according to embodiment 19, characterized in that the face plate is configured with a slot or opening to receive a portable memory card.

21. The system according to one of the preceding embodiments, characterized in that the system further comprises a detector to detect an amount of fragrance that is delivered into an airspace.

22. The system according to embodiment 21, characterized in that the detector is configured to provide feedback to the system such that the airspace is not continuously saturated with fragrance.

23. The system according to one of the preceding embodiments, characterized in that the cartridge assembly is replaceable and comprises a cartridge bottle and the collector assembly.

24. The system according to one of the preceding embodiments, characterized in that the system further comprises a cap to cover the opening of the nozzle.

25. The system according to embodiment 25, characterized in that the cap is threaded and comprises a plug.

26. The system according to one of the preceding embodiments, characterized in that the system further comprises a ceiling mount.

27. The system according to one of the embodiments 1 to 26, characterized in that the system further comprises a wall mount.

28. An apparatus for fragrancing air in an airspace outside of the apparatus, the apparatus comprising:
    a cartridge assembly;
    a collector assembly, comprising:
        a nozzle to receive compressed air;
        a collector bottom to receive liquid fragrance oil from the cartridge assembly; and
        an output orifice,
    wherein the collector assembly is configured to atomize the liquid fragrance oil from the cartridge assembly and diffuse a fragrance from the collector assembly through the output orifice, wherein the cartridge assembly is configured to hold the liquid fragrance oil, wherein the cartridge assembly is configured to interface with the collector assembly so that the liquid fragrance oil is drawn up into the collector bottom; and a top chassis assembly comprising an adjustable fan, wherein the adjustable fan is configured to interact with the diffused fragrance from the output orifice to force the diffused fragrance away from the apparatus, wherein the adjustable fan is configured to be fixed in a direction to send the diffused fragrance oil in the direction.

29. A fragrance diffusion apparatus for fragrancing air in an airspace outside of the apparatus, the apparatus comprising:

means for generating compressed air in the fragrance diffusion apparatus;

means for receiving liquid fragrance oil;

means for using the compressed air to atomize the liquid fragrance oil into a fragrance;

means for releasing the fragrance to the airspace outside of the apparatus, wherein an air pressure inside of the apparatus is greater than an air pressure outside of the apparatus;

means for generating an airstream with an adjustable fan positioned near the airspace outside of the apparatus;

means for assisting the release of the fragrance to the airspace outside of the apparatus by placing the released fragrance into the generated airstream; and means for adjusting a direction of the release of the fragrance by adjusting an angle of the adjustable fan in the apparatus to adjust a direction of the airstream.

Other modifications are within the scope of the following claims.

What is claimed is:

1. A system for fragrancing an air space comprising:

a cartridge assembly;

a collector assembly, comprising:

a nozzle to receive compressed air, a collector bottom to receive a fragrance liquid from the cartridge assembly, and an output orifice, wherein the collector assembly is configured to atomize the fragrance liquid from the cartridge assembly and diffuse a fragrance from the collector assembly through the output orifice, wherein the cartridge assembly is configured to hold the fragrance liquid, and wherein the cartridge assembly is configured to interface with the collector assembly so that the fragrance liquid is drawn up into the collector bottom; and a top chassis assembly comprising an adjustable fan, wherein the adjustable fan is configured to interact with the diffused fragrance from the output orifice to force the diffused fragrance away from the system at an airflow direction that is adjustable relative to the cartridge assembly and the collector assembly.

2. The system according to claim 1, further comprising a fan adjustment mechanism to fix the adjustable fan in a direction at a downward angle in the system.

3. The system according to claim 2, wherein the adjustable fan comprises an on opening for an output of a fan-forced airflow, wherein the system comprises a fan chassis at the output of the adjustable fan, and wherein the fan chassis is configured to channel the fan-forced airflow at the output of the adjustable fan.

4. The system according to claim 3, wherein the fan chassis comprises a slot, and wherein the slot in the fan chassis is configured to receive the output orifice from the collector assembly.

5. The system according to claim 4, further comprising:

a front housing with a front side, a backside, and an opening configured for receiving the fan chassis and the output orifice;

a back housing with a front side and a backside;

a hinge to connect the front and back housings at the backside of each of the front and back housings, wherein the front and back housings are configured to enclose the collector assembly, the cartridge assembly, and the top chassis assembly; and a locking mechanism on the front side of the front and back housings to lock the front and back housings at the front side upon closing the front and back housings.

6. The system according to claim 5, wherein the top chassis assembly comprises an interface to display a status of the system.

7. The system according to claim 5, wherein the top chassis assembly comprises an interface to receive user input for system settings or instructions.

8. The system according to claim 7, wherein the system further comprises a bottom chassis assembly that is configured to receive the collector assembly and the cartridge assembly.

9. The system according to claim 8,
wherein the bottom chassis assembly comprises:
a guide plate for receiving the collector assembly; and
a locking mechanism for securing the collector assembly in the bottom chassis assembly.

10. The system according to claim 9,
wherein the collector assembly comprises a guide plate that is configured to interface with the guide plate of the bottom chassis assembly so that the collector assembly is configured to be received into the bottom chassis in a predetermined direction.

11. The system according to claim 10, wherein the bottom chassis assembly comprises a muffler assembly that is configured to serve as an air filter and a noise muffler for the system.

12. The system according to claim 10, wherein the adjustable fan is configured to tilt at an angle from 0° to 30° downward from the system.

13. The system according to claim 12,
wherein the interface comprises a printed circuit board with components configured to receive and process the instructions for operations of the system.

14. The system according to claim 13,
wherein the instructions comprise at least one of a setting of a fan speed and a setting of a compressed air flow.

15. The system according to claim 13,
wherein the instructions comprise a schedule for delivering the fragrance outside the system, and
wherein the schedule comprises a duty cycle and a cycle length of the duty cycle.

16. The system according to claim 1,
wherein the nozzle comprises at least two o-rings, and
wherein the at least two o-rings differ in a size.

17. The system according to claim 1,
wherein the output orifice is configured to be detachable from the collector assembly, and
wherein the output orifice is configured to be attachable at an angle to the collector assembly.

18. An apparatus for fragrancing air in an airspace outside of the apparatus, the apparatus comprising:
a cartridge assembly;
a collector assembly, comprising:
a nozzle to receive compressed air,
a collector bottom to receive a fragrance liquid from the cartridge assembly, and
an output orifice,
wherein the collector assembly is configured to atomize the fragrance liquid from the cartridge assembly and diffuse a fragrance from the collector assembly through the output orifice, wherein the cartridge assembly is configured to hold the fragrance liquid, and wherein the cartridge assembly is configured to interface with the collector assembly so that the fragrance liquid is drawn up into the collector bottom; and
a top chassis assembly comprising an adjustable fan,
wherein the adjustable fan is configured to interact with the diffused fragrance from the output orifice to force the diffused fragrance away from the apparatus at an airflow direction that is adjustable relative to the cartridge assembly and the collector assembly, and
wherein the adjustable fan is configured to be fixed in a first direction to send the diffused fragrance in a first airflow direction relative to the cartridge assembly and the collector assembly.

19. The apparatus according to claim 18,
wherein the first direction is a direction that is oriented downward from the apparatus, and
wherein the adjustable fan is configured to tilt at an angle from 0° to 30° in the downward direction from the apparatus.

20. The apparatus according to claim 18, wherein the adjustable fan is configure to be fixed in a second direction that is different from the first direction to send the diffused fragrance in a second airflow direction relative to the cartridge assembly and the collector assembly, the second airflow direction being different from the first airflow direction.

21. A fragrance diffusion apparatus for fragrancing air in an airspace outside of the apparatus, the apparatus comprising:
means for generating compressed air in the fragrance diffusion apparatus;
means for receiving a fragrance liquid;
means for using the compressed air to atomize the fragrance liquid into a fragrance;
means for releasing the fragrance to the airspace outside of the apparatus, wherein an air pressure inside of the apparatus is greater than an air pressure outside of the apparatus;
means for generating an airstream with an adjustable fan positioned near the airspace outside of the apparatus;
means for assisting the release of the fragrance to the airspace outside of the apparatus by placing the released fragrance into the generated airstream; and
means for adjusting a direction of the release of the fragrance by adjusting an angle of the adjustable fan in the apparatus to adjust a direction of the airstream relative to the means for releasing the fragrance to the airspace.

22. A system for fragrancing an air space comprising:
a cartridge assembly;
a collector assembly, comprising:
a nozzle to receive compressed air,
a collector bottom to receive a fragrance liquid from the cartridge assembly, and
an output orifice,
wherein the collector assembly is configured to atomize the fragrance liquid from the cartridge assembly and diffuse a fragrance from the collector assembly through the output orifice, hold the fragrance liquid, and interface with the collector assembly so that the fragrance liquid is drawn up into the collector bottom;
a top chassis assembly comprising an adjustable fan and an opening for an output of a fan-forced inflow, the adjustable fan being configured to interact with the diffused fragrance from the output orifice to force the diffused fragrance away from the system;
a fan chassis at the output of the adjustable fan, the fan chassis being configured to channel the fan-forced airflow at the output of the adjustable fan and comprising a slot, the slot being configured to receive the output orifice from the collector assembly;
a fan adjustment mechanism configured to fix the adjustable fan in a direction at a downward angle in the system;
a front housing with a front side, a backside, and an opening configured for receiving the fan chassis and the output orifice;
a back housing with a front side and a backside;

a hinge configured to connect the front and back housings at the backside of each of the front and back housings, wherein the front and back housings are configured to enclose the collector assembly, the cartridge assembly, and the top chassis assembly;

a locking mechanism on the front side of the front and back housings configured to lock the front and back housings at the front side upon closing the front and back housings; and a bottom chassis assembly that is configured to receive the collector assembly and the cartridge assembly.

23. The system according to claim 22, wherein the bottom chassis assembly comprises:

a guide plate for receiving the collector assembly; and a locking mechanism for securing the collector assembly in the bottom chassis assembly.

24. The system according to claim 23, wherein the collector assembly comprises a guide plate that is configured to interface with the guide plate of the bottom chassis assembly so that the collector assembly is configured to be received into the bottom chassis in a predetermined direction.

25. The system according to claim 24, wherein the bottom chassis assembly comprises a muffler assembly that is configured to serve as an air filter and a noise muffler for the system.

26. The system according to claim 24, wherein the adjustable fan is configured to tilt at an angle from 0° to 30° downward from the system.

27. The system according to claim 26, wherein the top chassis assembly comprises an interface to receive user input for system setting or instructions, the interface comprising a printed circuit board with components configured to receive and process the instructions for operations of the system.

28. The system according to claim 27, wherein the instructions comprise at least one of a setting of a fan speed and a setting of a compressed air flow.

29. The system according to claim 27, wherein the instructions comprise a schedule for delivering the fragrance outside the system, and wherein the schedule comprises a duty cycle and a cycle length of the duty cycle.

* * * * *